(12) United States Patent
Seim

(10) Patent No.: US 8,055,339 B2
(45) Date of Patent: Nov. 8, 2011

(54) REVERSE PACING-MODE SWITCH

(75) Inventor: Gary T. Seim, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 457 days.

(21) Appl. No.: 11/734,120

(22) Filed: Apr. 11, 2007

(65) Prior Publication Data

US 2008/0255628 A1 Oct. 16, 2008

(51) Int. Cl.
*A61N 1/368* (2006.01)
(52) U.S. Cl. .................................. 607/9; 607/2; 607/17
(58) Field of Classification Search .................. 607/9, 2, 607/14, 17
See application file for complete search history.

(56) References Cited

U.S. PATENT DOCUMENTS

| | | |
|---|---|---|
| 4,561,442 A | 12/1985 | Vollmann et al. |
| 5,133,350 A | 7/1992 | Duffin |
| 5,144,949 A | 9/1992 | Olson |
| 5,318,594 A | 6/1994 | Limousin et al. |
| 5,643,326 A | 7/1997 | Weiner et al. |
| 5,683,426 A | 11/1997 | Greenhut et al. |
| 6,397,105 B1 | 5/2002 | Bouhour et al. |
| 6,772,005 B2 | 8/2004 | Casavant et al. |
| 7,020,524 B1 * | 3/2006 | Bradley ........................ 607/27 |
| 7,257,442 B2 | 8/2007 | Kramer et al. |
| 2003/0078627 A1 | 4/2003 | Casavant et al. |
| 2003/0144698 A1 * | 7/2003 | Ujhelyi et al. .................... 607/4 |
| 2004/0143299 A1 | 7/2004 | Casavant et al. |
| 2004/0260349 A1 | 12/2004 | Stroebel |
| 2005/0055059 A1 | 3/2005 | Betzold et al. |
| 2005/0197674 A1 | 9/2005 | McCabe et al. |
| 2005/0267538 A1 | 12/2005 | Kramer et al. |
| 2006/0167508 A1 * | 7/2006 | Boute et al. ........................ 607/9 |
| 2007/0073352 A1 * | 3/2007 | Euler et al. ...................... 607/23 |
| 2007/0106334 A1 * | 5/2007 | Ziegler et al. .................... 607/9 |

FOREIGN PATENT DOCUMENTS

| | | |
|---|---|---|
| WO | WO-2006/116550 A1 | 11/2006 |
| WO | WO-2008/127614 | 10/2008 |

OTHER PUBLICATIONS

"Pacemaker System Guide—Pulsar Max™ II", *Guidant Models 1280/1181/1180*, (Oct. 25, 1999), 3 pgs.

(Continued)

*Primary Examiner* — Carl H Layno
*Assistant Examiner* — Jennifer Stewart
(74) *Attorney, Agent, or Firm* — Schwegman, Lundberg & Woessner, P.A.

(57) ABSTRACT

A device comprises a cardiac contraction sensing circuit, a timer circuit, an electrical stimulation circuit, and a controller. The timer circuit provides a time duration of an atrial-atrial interval between successive atrial contractions, a ventricular-ventricular interval between successive ventricular contractions, and an atrial-ventricular (A-V) interval between an atrial contraction and a same cardiac cycle ventricular contraction. The controller includes an event detection module and a pacing module. The event detection module is configured for determining whether A-V block events are sustained over multiple cardiac cycles. The pacing module is configured for providing pacing therapy according to a primary pacing mode that includes AAI(R) mode with independent VVI backup mode, and for switching the pacing therapy to a secondary pacing mode if A-V block events are sustained over multiple cardiac cycles. Other devices and methods are described.

31 Claims, 8 Drawing Sheets

OTHER PUBLICATIONS

"Performance Notes—Interactions Between Cardiac Pacing and Ventricular Arrhythmia Initiation"*Medtronic CRDM Product Performance Report*, (Aug. 22, 2006), 1 pg.

"Virtuoso™ DR/VR D154AWG/D 154VWC—Implantable Cardioverter Defibrillator Systems With Opt./VoI™", *Medtronic Reference Manual*, (prior to Mar. 27, 2007), 239-244.

Gray, C. J., et al., "Inappropriate Application of "Managed Ventricular Pacing" in a Patient With Brugada Syndrome Leading to Polymorphic Ventricular Tachycardia, Ventricular Fibrillation, and Implantable Cardioverter Defibrillator Shocks", *Heart Rhythm*, vol. 3, Issue 5S, (Abstract P1-89),(May, 2006),1 pg.

Sharma, A. D., et al., "Percent Right Ventricular Pacing Predicts Outcomes in the DAVID Trial", *Heart Rhythm*, 2(8), (2005), 1547-5271.

Steinberg, J. S., et al., "The Clinical Implications of Cumulative Right Ventricular Pacing in the Multicenter Automatic Defibrillator Trial II", *Journal of Cardiovascular Electrophysiology*, 16(4), (Apr. 2005), 359-365.

The DAVID Trial Investigators, "Dual-Chamber Pacing or Ventricular Backup Pacing in Patients With an Implantable Defibrillator", *JAMA*, 288(24), (Dec. 25, 2002), 3115-3123.

"International Application Serial No. PCT/US2008/004629, International Search Report mailed Aug. 21, 2008", 5 pgs.

"International Application Serial No. PCT/US2008/004629, Written Opinion mailed Aug. 21, 2008", 8 pgs.

"Australian Application Serial No. 2008239688, First Examiner Report mailed Aug. 10, 2010", 5 pgs.

"Australian Application Serial No. 2008239688, Response filed Feb. 23, 2011 to First Examiner Report mailed Aug. 10, 2010", 31 pgs.

"European Application Serial No. 08742722.5, Office Action mailed Jan. 27, 2011", 3 pgs.

"International Application Serial No. PCT/US2008/004629, International Preliminary Report on Patentability mailed on Oct. 22, 2009", 9 pgs.

"Australian Application Serial No. 2008239688, Examiner Report mailed Mar. 24, 2011", 4 pgs.

"Australian Application Serial No. 2008239688, Response filed May 24, 2011 to Subsequent Examiners Report mailed Mar. 24, 2011", 18 pgs.

"Eurppean Application Serial No. 08742722.5, Response flied May 20, 2011 to Office Action mailed Jan. 27, 2011", 13 pgs.

* cited by examiner

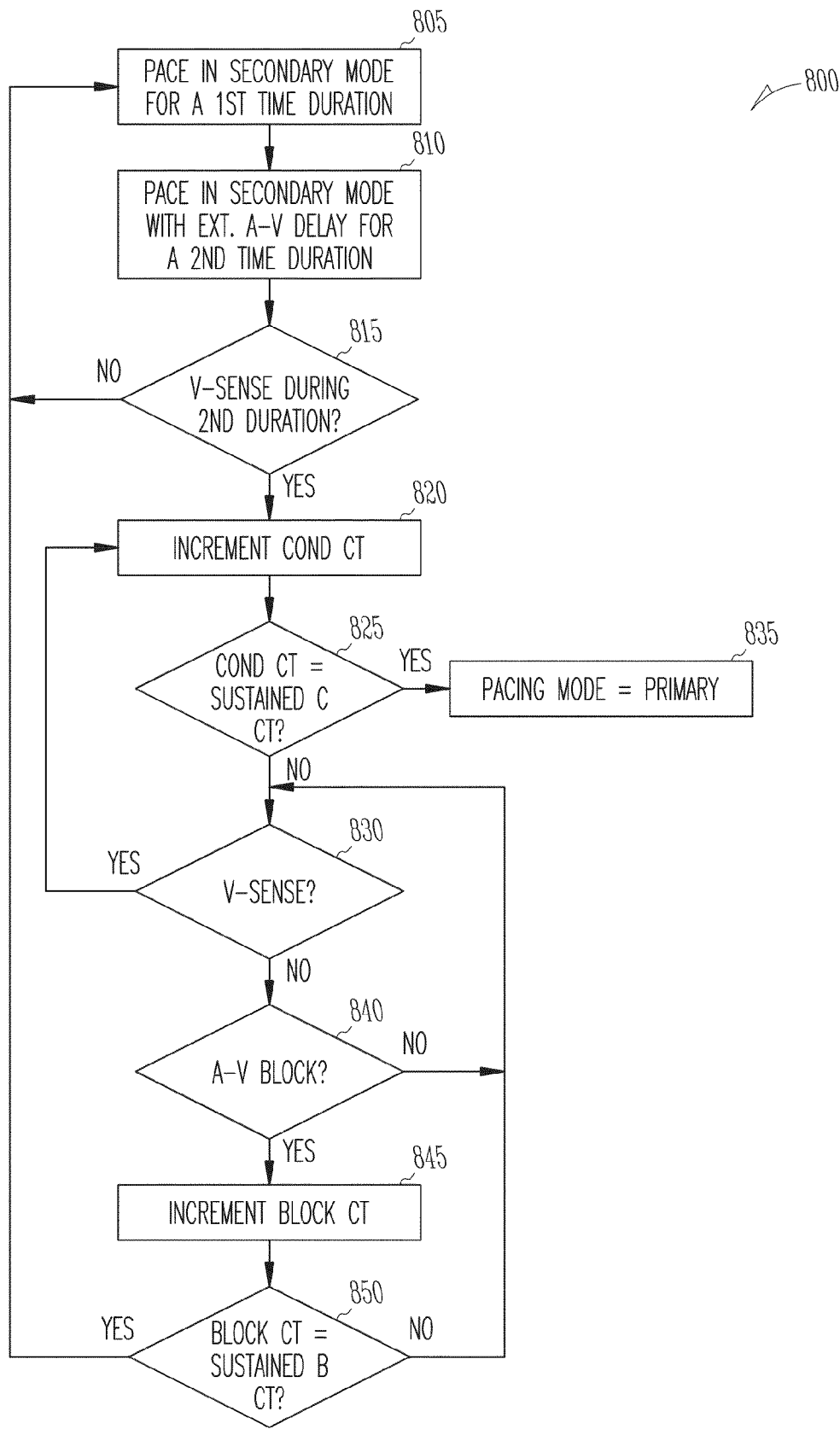

REVERSE PACING-MODE SWITCH

FIELD OF THE INVENTION

The field generally relates to implantable medical devices and, in particular, but not by way of limitation, to systems, devices, and methods for providing cardiac arrhythmia therapy to a subject.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Several types of CFMs provide pacing to one or more ventricles of a patient or subject under a conventional dual chamber DDD pacing mode. In DDD mode, the CFM device is able to provide pacing and sensing to both the atrium and ventricle, and is able to coordinate activity in one heart chamber according to events in the other. For example, the CFM device is able to pace the ventricle according to a timing relationship of paced or sensed events in the atrium. However, unnecessary ventricular pacing may be associated with an increased risk of heart failure and atrial fibrillation in patients with dual chamber CFM devices such as pacemakers and ICDs.

SUMMARY

This document relates generally to systems, devices, and methods for providing cardiac arrhythmia therapy to a subject. A device example includes a cardiac contraction sensing circuit, a timer circuit, an electrical stimulation circuit and a controller. The timer circuit provides a time duration of an atrial-atrial (A-A) interval between successive atrial contractions, a ventricular-ventricular (V-V) interval between successive ventricular contractions, and an atrial-ventricular (A-V) interval between an atrial contraction and a same cardiac cycle ventricular contraction. The controller includes an event detection module and a pacing module. The event detection module is configured for determining whether A-V block events are sustained over multiple cardiac cycles and a pacing module. The pacing module is configured for providing pacing therapy according to a primary pacing mode that includes AAI(R) mode with independent VVI backup mode, and for switching the pacing therapy to a secondary pacing mode if A-V block events are sustained over multiple cardiac cycles.

A method example includes sensing A-A intervals between successive atrial contractions in an atrium and V-V intervals between successive ventricular contractions in a ventricle, providing pacing therapy according to a primary pacing mode, determining whether A-V block events are sustained over multiple cardiac cycles, and switching the pacing therapy to a secondary pacing mode if A-V block events are sustained over multiple cardiac cycles. The primary mode includes pacing at least one atrium when an A-A interval exceeds an atrial lower rate limit (LRL) interval and pacing at least one ventricle, without regard to events occurring in the atrium, when a V-V interval exceeds a ventricular LRL interval, wherein the ventricular LRL interval is longer than the atrial LRL interval. The secondary pacing mode includes pacing the ventricle when an A-V interval between an atrial contraction and a same cardiac cycle ventricular contraction exceeds a first A-V delay interval.

This summary is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

FIG. 8 shows an example of a method to implement A-V search hysteresis.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
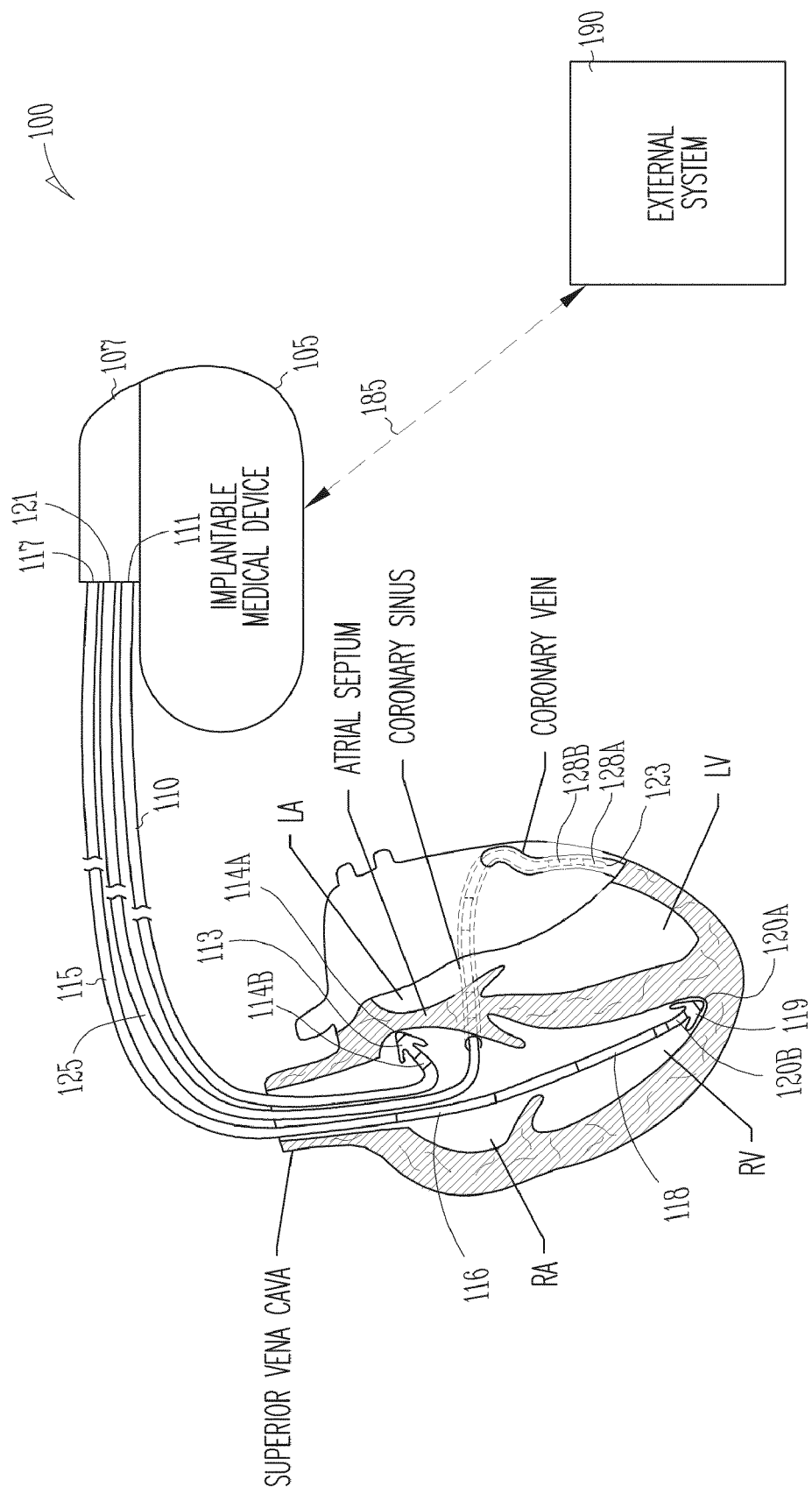
FIG. 1 is an illustration of portions of a system that uses an implantable medical device (IMD).

FIG. 1 is an illustration of portions of a system 100 that uses an implantable medical device (IMD) 105. Examples of IMD 105 include, without limitation, a, pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." System 100 also typically includes an IMD programmer or other external system 190 that communicates one or more wireless signals 185 with the IMD 105, such as by using radio frequency (RF) or one or more other telemetry signals.

The example shown includes right atrial (RA) lead 110 having a proximal end 111 and a distal end 113. Proximal end 111 is coupled to a header connector 107 of the IMD 105. Distal end 113 is configured for placement in the RA in or near the atrial septum. RA lead 10 may include a pair of bipolar electrodes, such as an RA tip electrode 114A and an RA ring electrode 114B. RA electrodes 114A and 114B are incorporated into the lead body at distal end 113 for placement in or near the atrial septum, and are each electrically coupled to IMD 105 through a conductor extending within the lead body. The RA lead is shown placed in or near the atrial septum, but the RA lead may be placed in the atrial appendage.

The example shown also includes right ventricular (RV) lead 115 having a proximal end 117 and a distal end 119. Proximal end 117 is coupled to header connector 107. Distal end 119 is configured for placement in the RV. RV lead 115 may include one or more of a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA and/or the superior vena cava. Defibrillation electrode 118 is incorporated into the lead body near distal end 119 for placement in the RV. RV electrodes 120A and 120B may form a bipolar electrode pair and are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or an electrode formed on the can of IMD 105 allow for delivery of cardioversion/defibrillation pulses to the heart.

RV tip electrode 120A, RV ring electrode 120B, and/or an electrode formed on the can of IMD 105 allow for sensing an RV electrogram indicative of RV depolarizations and delivering RV pacing pulses. RA tip electrode 114A, RA ring electrode 114B, and/or an electrode formed on the can of IMD 105 allow for sensing an RA electrogram indicative of RA depolarizations and delivering RA pacing pulses. Sensing and pacing allows the IMD 105 to adjust timing of the heart chamber contractions. In some device examples, IMD 105 can adjust the timing of ventricular contractions with respect to the timing of atrial contractions delay by sensing a contraction in the RA and pacing the RV at the desired atrial-ventricular (AV) delay time. This occurs if the device is providing therapy according to DDD mode.

Also shown is a left ventricular (LV) lead 125. LV lead 125 is a coronary pacing and/or sensing lead that includes an elongate lead body having a proximal end 121 and a distal end 123. Proximal end 121 is coupled to header connector 107. Distal end 123 is configured for placement or insertion in the coronary vein. LV lead 125 may include an LV tip electrode 128A and an LV ring electrode 128B. The distal portion of LV lead 125 is configured for placement in the coronary sinus and coronary vein such that LV electrodes 128A and 128B are placed in the coronary vein. LV electrodes 128A and 128B may form a bipolar electrode pair and are incorporated into the lead body at distal end 123 and each electrically coupled to IMD 105 through a conductor extending within the lead body. LV tip electrode 128A, LV ring electrode 128B, and/or an electrode formed on the can of IMD 105 allow for sensing an LV electrogram indicative of LV depolarizations and delivering LV pacing pulses.

Other forms of electrodes include meshes and patches, which may be applied to one or more portions of heart, or which may be implanted in one or more other areas of the body to help "steer" electrical current produced by IMD 105 in FIG. 1. The IMDs may be configured with a variety of electrode arrangements, including transvenous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes). Monitoring of electrical signals related to cardiac activity may provide early, if not immediate, diagnosis of cardiac disease.

Unnecessary ventricular pacing may be associated with an increased risk of heart failure and atrial fibrillation in patients with dual chamber CFM devices. Atrioventricular (AV) delay refers to the delay between an atrial event (either paced or sensed) and a ventricular pace. With a fixed AV delay, if an intrinsic ventricular depolarization is not sensed by the expiration of the AV delay, a dual chamber CFM will pace the ventricle following an atrial event at the expiration of the AV delay. A dynamic AV delay allows the AV delay to shorten with the atrial rate, such as when the patient is exercising. Allowing a CFM device to search for an intrinsic ventricular pulse during the AV delay may reduce unnecessary ventricular pacing.

CFM devices are able to provide pacing therapy in different pacing modes, such as the DDD mode for example. In some implementations of DDD mode, the ventricle is paced after expiration of a fixed or dynamic AV delay. AAI mode is a single chamber pacing mode that provides atrial chamber pacing and sensing. After an atrial event (sensed or paced) occurs, the atrium is paced if an atrial event to atrial event (A-A) interval will exceed an atrial lower rate limit (LRL) time duration, i.e., the atrium is paced if an atrial lower rate limit (LRL) time interval expires before a sensed atrial depolarization is detected. VVI mode is a single chamber pacing mode that provides ventricular chamber pacing and sensing. After a ventricular event (sensed or paced) occurs, the ventricle is paced if a ventricular event to ventricular event (V-V) interval will exceed a ventricular lower rate limit (LRL) time duration, i.e., the ventricle is paced if a ventricular LRL time interval expires before a sensed ventricular depolarization is detected. Providing pacing therapy according to AAI mode with a CFM device and providing backup VVI mode pacing that is independent of the AAI pacing may reduce unnecessary ventricular pacing.

Figure 2:
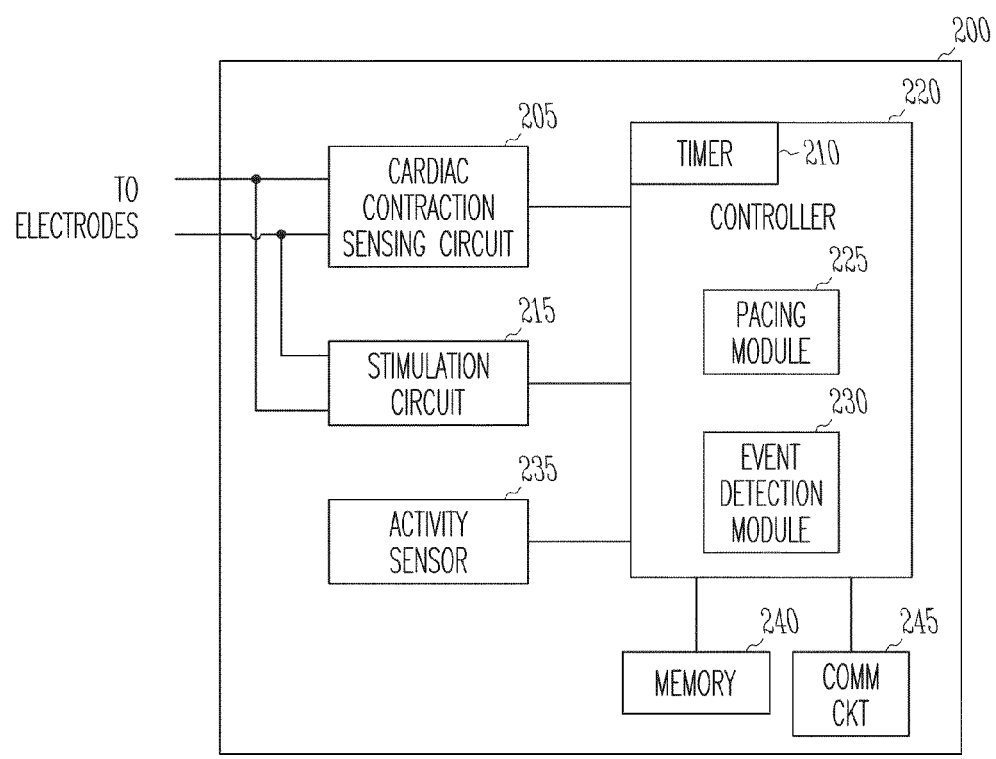
FIG. 2 is a block diagram of an example of portions of a device to provide therapy for cardiac arrhythmia.

FIG. 2 is a block diagram of an example of portions of a device 200 to provide therapy for cardiac arrhythmia. The device includes at least one implantable cardiac contraction sensing circuit 205, a timer circuit 210, an electrical stimulation circuit 215, and a controller 220 that is communicatively coupled to the cardiac contraction sensing circuit 205, the timer circuit 210, and the electrical stimulation circuit 215. The cardiac contraction sensing circuit 205 provides a sensed contraction signal from an atrium and a sensed contraction signal from a ventricle. The timer circuit 210 uses the contraction signal from the atrium to determine a time duration of atrial-atrial (A-A) intervals between successive atrial contractions, and uses the contraction signal from the ventricle to determine a time duration of ventricular-ventricular (V-V) intervals between successive ventricular contractions. The timer circuit 210 uses the contraction signals from the atrium and ventricle to determine a time duration of an atrial-ventricular (A-V) interval between an atrial contraction and a same cardiac cycle ventricular contraction. The electrical stimulation circuit 215 provides pacing electrical stimulation energy to at least one implantable electrode in the atrium and at least one implantable electrode in the ventricle. In some examples, the electrical stimulation circuit 215 provides pacing electrical stimulation energy to at least one electrode in the right ventricle and one electrode in the left ventricle.

The controller 220 may include a digital signal processor, application specific integrated circuit (ASIC), microprocessor, or other type of processor, interpreting or executing instructions in software or firmware. In some examples, the controller 220 may include a state machine or sequencer that is implemented in hardware circuits. The controller 220 may include any combination of hardware, firmware, or software. The controller 220 includes one or modules to perform the functions described herein. A module may include software, hardware, firmware or any combination thereof. Multiple functions may be performed in one or more modules.

The controller 220 includes a pacing module 225. The pacing module 225 provides pacing therapy according to a primary pacing mode and a secondary pacing mode. In some examples of the primary pacing mode, the pacing module 225 provides pacing in AAI mode to an atrium, and provides pacing in VVI mode to at least one ventricle. The VVI pacing is independent of the AAI pacing in that the VVI pacing is executed without regard to any event (sensed or paced) occurring in the atrium. There is no tracking of atrial depolarizations by the ventricle in the ventricular pacing mode. In this way the device 200 acts as if there are two independent single chamber devices providing pacing therapy to two different heart chambers. However, the ventricular LRL interval is longer than the atrial LRL interval. For example, the ventricular LRL interval may be set to 1.333 s (corresponding to a lower rate of 45 bpm) while the atrial LRL interval is set to 1.0 s (corresponding to a lower rate of 60 bpm). The primary pacing mode is then AAI mode with an independent backup VVI mode with the ventricular LRL set 15 bpm lower than the atrial LRL. Having a long ventricular LRL interval promotes the reduction of ventricular pacing for patients with normal A-V conduction.

Figure 3:
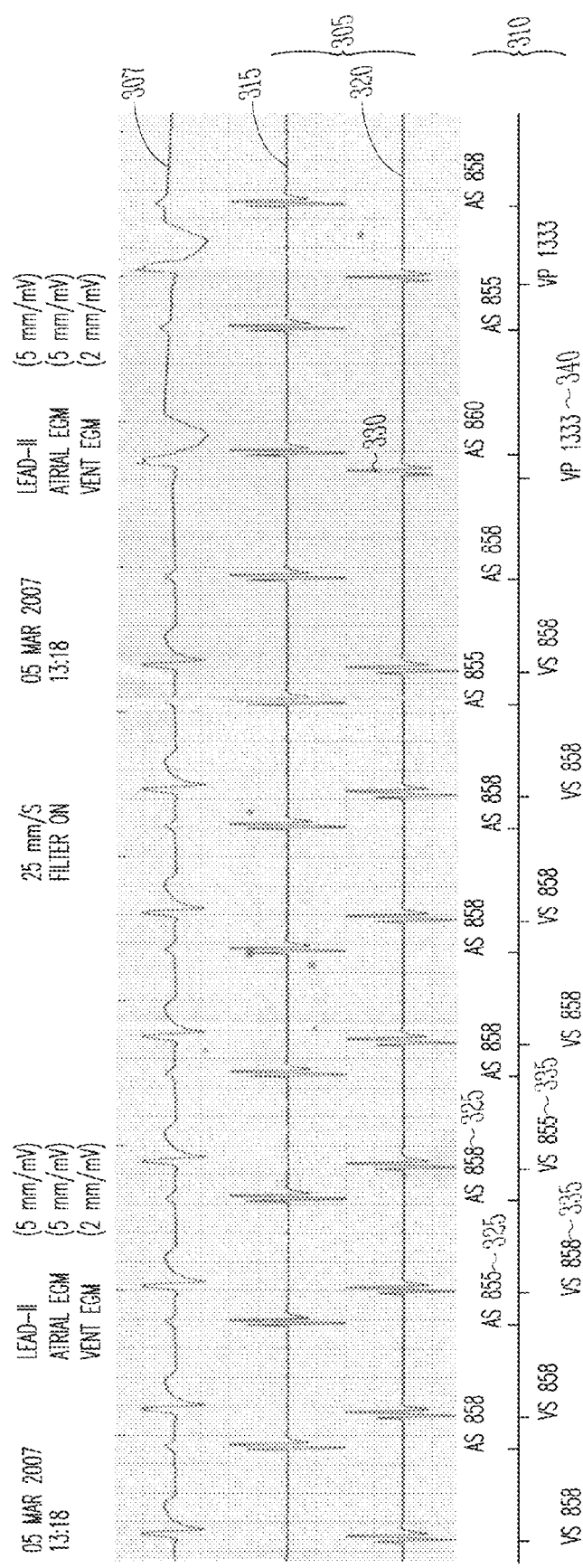
FIG. 3 shows simulated waveforms, including sensed and paced events, and markers corresponding to a primary pacing mode.

FIG. 3 shows simulated waveforms 305, including sensed and paced events, simulated electrocardiogram (ECG) 307, and markers 310 corresponding to the primary pacing mode. The first waveform 315 shows atrial events. In the first waveform, intrinsic atrial contractions are occurring with an interval of 0.858 s, or a rate of about 52 bpm. The atrial markers 325 indicate the sensed atrial events. The second waveform 320 shows ventricular events. The first several events of the waveform 320 show that conduction of the depolarization from atrium to the ventricle (A-V conduction) occurs and the ventricle is depolarizing at the same rate as the atrium (rate interval of 0.858 s). The ventricular markers 335 indicate the ventricular sensed events.

The ventricular LRL is set to 45 bpm, or an interval of 1.333 s, and is set lower than the atrial LRL. Paced ventricular event 330 shows where the depolarization of the atrium is not conducted to the ventricle (A-V block). The ventricle is paced at the ventricular LRL. The ventricular marker 340 indicates a V-paced event. The second waveform 320 shows intrinsic conduction developing into complete heart block. The ventricular pace events after the block do not exhibit any atrial tracking.

In some examples, the device 200 in FIG. 2 includes an activity sensor 235 coupled to the controller 220. An example of an activity sensor 235 is an accelerometer. The pacing module 225 provides pacing to an atrium in a rate responsive mode or AAI(R) mode. In AAI(R) mode, the controller 220 adjusts the atrial rate according to the output of the activity sensor. The pacing module 225 paces the atrium when an A-A interval exceeds an activity sensor indicated atrial rate interval. The primary pacing mode is then AAI(R) mode with an independent backup VVI mode. Atrial tracking is not provided and the activity sensor output does not increase the ventricular rate because by definition atrial tracking is a feature of DDD(R) mode or VDD(R) mode. In some examples, the primary pacing mode is AAI(R) mode with an independent backup VVI(R) mode. The independent VVI(R) activity sensor indicated ventricular rate interval is longer than the activity sensor indicated AAI(R) atrial rate interval.

In some examples, the pacing module 225 provides DDD pacing as the secondary pacing mode and programmed DDD parameters are used. In certain examples, the pacing module 225 provides DDD(R) pacing as the secondary pacing mode. The pacing module 225 switches pacing modes from the primary pacing mode to the secondary pacing mode if A-V block events are sustained over multiple cardiac cycles. The secondary pacing mode includes pacing the at least one ventricle when an atrial-ventricular contraction (A-V) interval exceeds a first A-V delay interval specified in the device 300.

The controller 220 includes an event detection module 230 that determines whether atrial-ventricular (A-V) block events are sustained over multiple cardiac cycles. In some examples, the event detection module 230 declares an A-V block event if the ventricular LRL interval is exceeded without a sensed ventricular event occurring. For example, in FIG. 3, an A-V block event is declared when the ventricular LRL interval is exceeded and an RV pace occurs as indicated by the paced ventricular event 330 and ventricular marker 340.

In some examples, the event detection module 230 declares an A-V block event if a V-V interval is sensed that is longer than the atrial LRL interval by a specified threshold value and shorter than the ventricular LRL interval. For example, in FIG. 4 the atrium is being paced at the atrial LRL (45 bpm, or an interval of 1.333 s) and the ventricular LRL is set to 30 bpm (2.0 s). If a sensed V-V interval is shorter than the 2.0 s ventricular LRL interval but longer than the 1.333 s atrial LRL interval by a specified threshold time value, the event detection module 230 declares an A-V block event. In some examples, the device 200 includes an activity sensor 235 and the event detection module 230 may declare an A-V block event if a V-V interval is sensed that is longer than an activity sensor indicated atrial rate interval by a specified threshold value and shorter than the ventricular LRL interval.

The specified threshold time may be zero, but it is preferable to have a non-zero threshold to allow for possible jitter in A-V conduction or jitter in the sensing by the device 200. As an illustrative example, the specified threshold time may be one millisecond (1 ms). An A-V block event would be declared if the V-V interval is longer than 1.334 s. In another illustrative example, the specified threshold time may be 150 ms. An A-V block event would be declared if the V-V interval is longer than 1.483 s.

The event detection module 230 declares A-V block events and declares when the A-V block events are sustained. In some examples, the event detection module 230 declares A-V block events to be sustained when an A-V blocking event is declared in X out of Y consecutive V-V intervals, wherein X and Y are integers and X is less than or equal to Y. In some examples, the event detection module 230 includes an X out of Y counter to detect that a certain degree of A-V block is occurring. As an illustrative example, Y is ten and X is two. The event detection module 230 tracks how many A-V block events have occurred in the last ten V-V intervals, e.g., the event detection module 230 sets up a rolling window that looks at the last ten V-V intervals where the intervals include sensed and paced events. A 2 out of 10 counter will detect conditions where a patient has an A-V block event one out of five V-V intervals. (This can also be viewed as 5:4 block. In 5:4 block, the patient has 4 A-V conduction events for every 5 atrial depolarizations. Without a pacemaker, there would be 4 V-V intervals for every 5 A-A intervals. A pacemaker provided ventricular pace event provides the fifth V-V interval.) The 2 out of 10 counter will not detect conditions where the patient has an A-V conduction event one out of six V-V intervals. (This can be viewed as 6:5 block. In 6:5 block, the patient has 5 A-V conduction events for every 6 atrial depolarizations.) Of course, higher degrees of A-V conduction block will be detected with the 2 out of 10 counter, such as if the patient has an A-V conduction event in one out of two V-V intervals. (This can be viewed as 2:1 block. In 2:1 block, the patient has 1 A-V conduction events for every 2 atrial depolarizations.)

In some examples, the event detection module 230 includes an A-V block event counter to count the number of block events after the X out of Y counter initially registers an A-V block. The A-V block event counter is used to track how long the detected A-V block has occurred before a mode switch is performed. In the example, if there are less than two A-V block events out of the last ten V-events, the event detection module 230 sets the A-V block event counter to zero. If there are two or more A-V block events out of the last ten V-events, the event detection module 230 declares that sustained A-V block is detected and activates an indication of sustained A-V block. The indication may include sending a signal to the pacing module 225 or setting a flag in a memory. When sustained A-V block is detected, the pacing module 225 switches to the secondary pacing mode. The values of X and Y can be changed according to how strongly the caregiver wishes to promote V-sensing. For example, increasing X to three makes it slightly more difficult for sustained A-V block to be declared.

Figure 4:
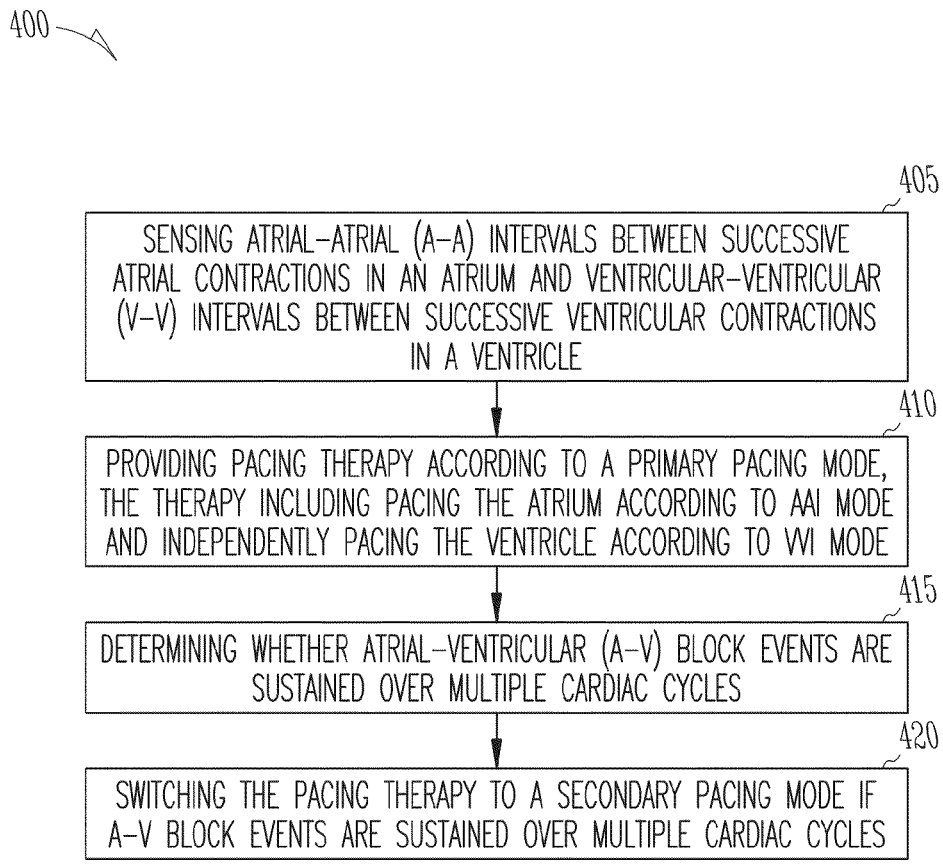
FIG. 4 is a flow diagram of an example of a method to provide therapy for cardiac arrhythmia.

FIG. 4 is a flow diagram of an example of a method 400 to provide therapy for cardiac arrhythmia. At block 405, A-A intervals between successive atrial contractions are sensed in an atrium, and V-V intervals between successive ventricular contractions in a ventricle. At 410, pacing therapy is provided to a subject according to a primary pacing mode. In some examples, the primary pacing mode includes pacing the atrium according to the AAI pacing mode (e.g., pacing at least one atrium when an A-A interval exceeds an atrial LRL interval), and independently pacing at least one ventricle according to VVI mode without regard to events occurring in the atrium (e.g., pacing the ventricle when a V-V interval exceeds a ventricular LRL interval and the ventricular LRL interval is longer than the atrial LRL interval). In some examples, the primary pacing mode includes pacing the atrium according to an AAI(R) pacing mode (e.g., pacing an atrium when an A-A interval exceeds an activity sensor indicated atrial rate interval) with backup independent VVI pacing. In some examples, the primary pacing mode is AAI(R) mode with an independent backup VVI(R) pacing.

At block 415, it is determined whether A-V block events are sustained over multiple cardiac cycles. At 420, the pacing therapy is switched to a secondary pacing mode if A-V block events are sustained over multiple cardiac cycles. In some examples, the secondary pacing mode includes the DDD pacing mode (e.g., pacing the ventricle when an atrial-ventricular (A-V) interval between an atrial contraction and a same cardiac cycle ventricular contraction exceeds a first A-V delay interval).

Figure 5:
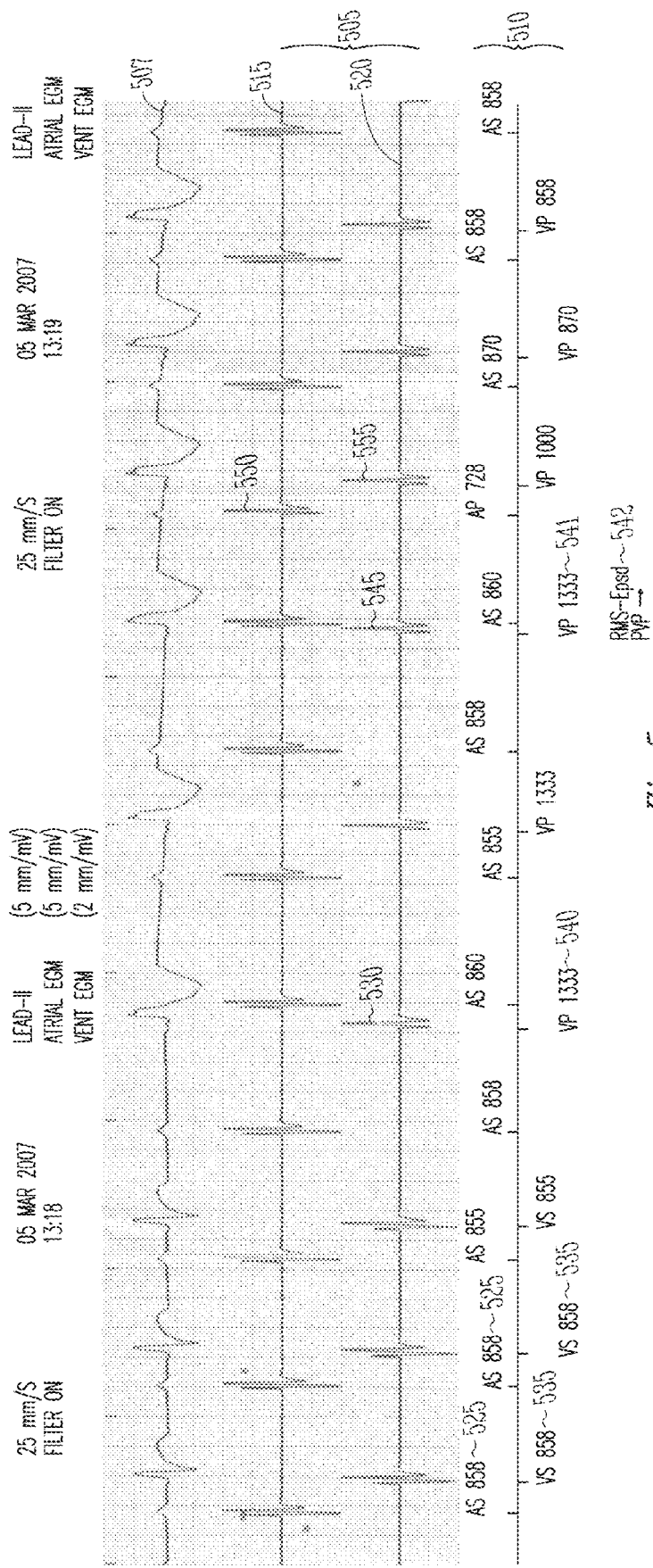
FIG. 5 shows simulated waveforms, including sensed and paced events, and markers showing an example of a switch from a primary pacing mode to a secondary pacing mode.

FIG. 5 shows simulated waveforms 505, including sensed and paced events, simulated ECG 507, and markers 510 showing an example of a switch from the primary pacing mode to the secondary pacing mode. In the example, the primary pacing mode is AAI with independent back-up VVI and the secondary pacing mode is DDD. The waveforms include an atrial waveform 515 and a ventricular waveform 520. The atrial waveform 515 shows intrinsic atrial contractions are occurring with an interval of 0.858 s. The atrial markers 525 indicate the sensed atrial events.

As in FIG. 3, the first several events of the ventricular waveform 520 show that conduction of the depolarization from atrium to the ventricle (A-V conduction) occurs and the ventricle is depolarizing at the same rate as the atrium (rate interval of 0.858 s). The ventricular markers 535 indicate the ventricular sensed events. Paced ventricular event 530 shows where the depolarization of the atrium is not conducted to the ventricle (A-V block). The ventricle is paced at the ventricular LRL and the ventricular marker 540 indicates pacing at the ventricular LRL of 45 bpm. The ventricular waveform 520 corresponds to complete heart block and the ventricular pace events do not exhibit any atrial tracking.

The third paced ventricular event 545 corresponds to a third A-V block event as indicated by the ventricular marker 541. Sustained A-V block is declared after the third V-pace. A reverse mode switch (RMS) episode marker 542 is displayed and the pacing therapy is switched to the secondary mode, here the DDD mode. Atrial depolarization 550 and ventricular depolarization 555 correspond to DDD mode. The ventricular depolarization 555 tracks the atrial depolarization 550 with an A-V delay of about 170 ms.

Figure 6:
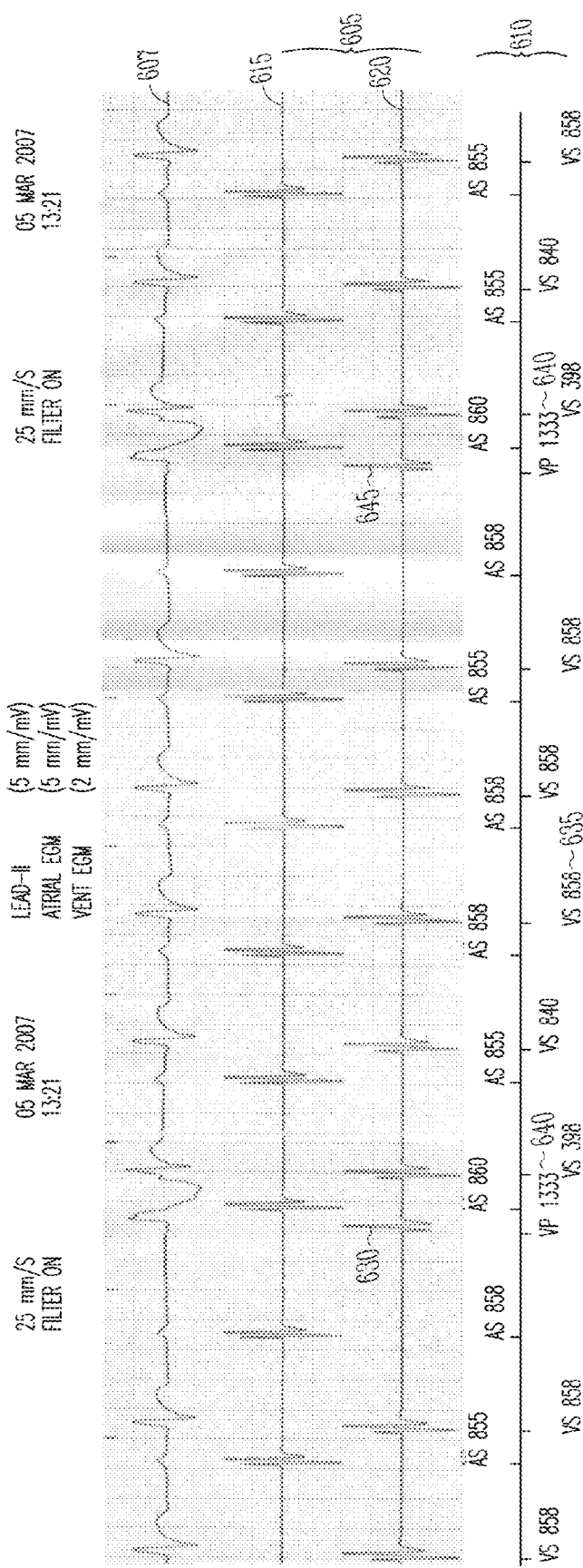
FIG. 6 shows simulated waveforms, including sensed and paced events, and markers showing an example of intermittent A-V block while pacing according to a primary pacing mode.

FIG. 6 shows simulated waveforms 605, including sensed and paced events, simulated ECG 607, and markers 610 showing an example of intermittent A-V block while pacing according to a primary pacing mode of AAI mode with independent VVI backup mode. The example corresponds to 6:5 heart block (the patient experiences 5 A-V conduction events out of 6 atrial depolarizations). The waveforms include an atrial waveform 615 and a ventricular waveform 620. The atrial waveform 615 shows intrinsic atrial contractions are occurring with an interval of 0.858 s. Ventricular depolarizations 630 and 645 correspond to A-V block events as indicated by the ventricle pace markers 640. Sustained A-V block is not declared after the second V-pace because the A-V block detector counter is being reset. A reverse mode switch (RMS) episode marker is not displayed and the pacing therapy is not switched to a secondary mode.

Figure 7:
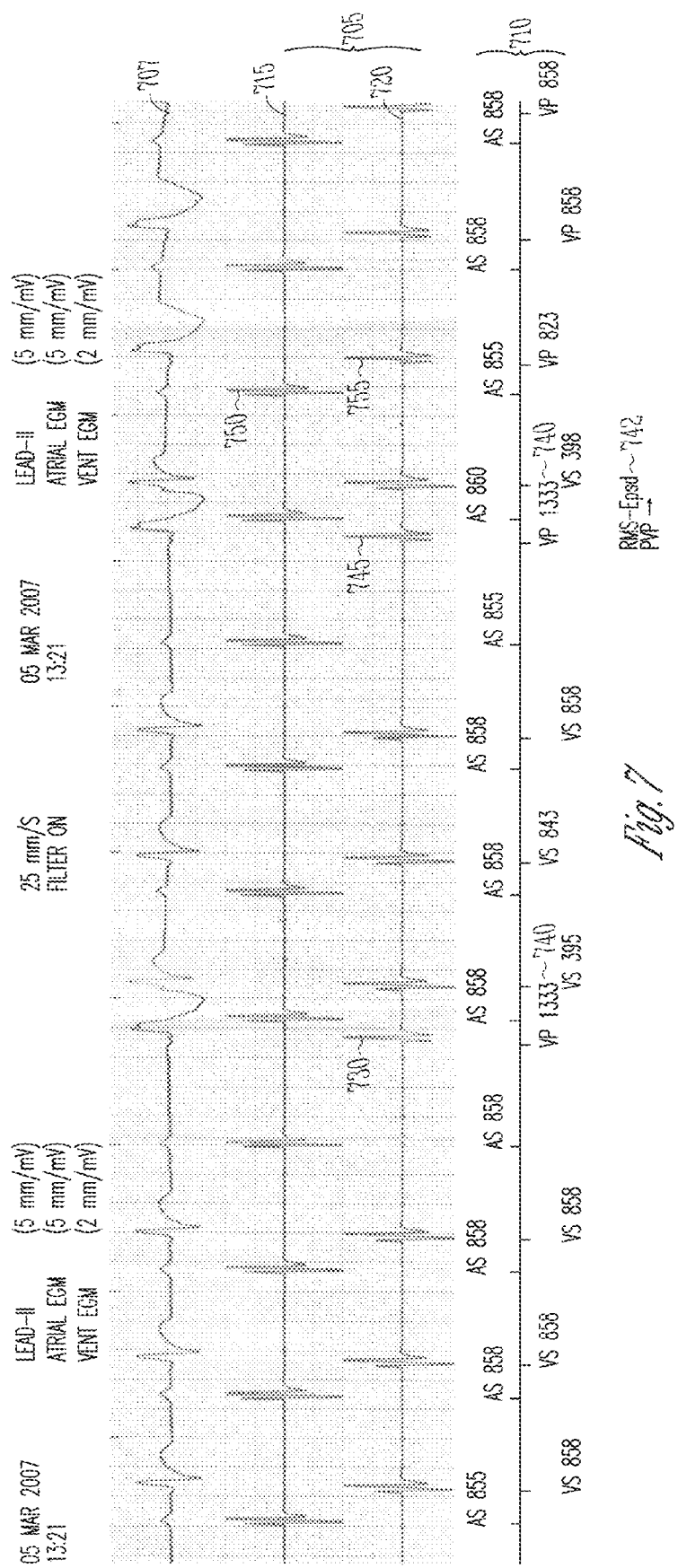
FIG. 7 shows simulated waveforms, including sensed and paced events, and markers showing an example of increased intermittent A-V block that causes a switch from a primary pacing mode to a secondary pacing mode.

FIG. 7 shows simulated waveforms 705, including sensed and paced events, simulated ECG 707, and markers 710 showing an example of increased intermittent A-V block that causes a switch from a primary pacing mode to a secondary pacing mode. The example shows an episode of 4:3 heart block (the patient experiences 3 A-V conduction events for every 4 atrial depolarizations). The waveforms 705 include an atrial waveform 715 and a ventricular waveform 720, and the primary pacing mode is AAI mode with independent VVI backup mode. Ventricular depolarizations 730 and 745 correspond to A-V block events as indicated by the ventricle pace markers 740. Sustained A-V block is declared after the second V-pace. An RMS episode marker 742 is displayed and the pacing therapy is switched to the secondary mode. Atrial depolarization 750 and ventricular depolarization 755 correspond to a DDD mode. The ventricle is paced with an A-V delay after the atrial depolarization 750.

Returning to the device 200 in FIG. 2, the pacing module 225 may switch back to the primary pacing mode after providing pacing therapy in the secondary pacing mode for only a specified number of cardiac cycles. If A-V block is sustained, the device 200 may periodically switch back and forth between the primary and secondary pacing modes. If the primary mode is AAI/AAI(R) with VVI backup and the secondary pacing mode is DDD/DDD(R), the patient may sense the mode switching. The pacing module 225 may switch and stay in the secondary mode if a specified number of mode switches are made within a specified period of time. The device 200 will stay in secondary mode if A-V block is sustained. If the secondary mode is DDD/DDD(R), intrinsic ventricular contractions will not be promoted by the device. It is preferable to switch from the secondary mode to the primary mode when the restoration of some level of A-V conduction is detected.

According to some examples, the pacing module 225 may switch from the secondary pacing mode back to the primary pacing mode if the pacing module 225 detects that A-V conduction events are sustained. In certain examples, the pacing module 225 switches from DDD or DDD(R) pacing to AAI with backup VVI, or AAI(R) with backup VVI, or AAI(R) with backup VVI(R) to promote more intrinsic ventricular contractions. The event detection module 230 determines whether A-V conduction events are sustained over multiple cardiac cycles. This may be referred to as A-V search hysteresis and the pacing module 225 uses an A-V search hysteresis feature to allow intrinsic ventricular contractions to be sensed.

FIG. 8 shows an example of a method 800 that may be used in implementing A-V search hysteresis and sustained A-V conduction detection in the pacing module 225 and event detection module 230. At block 805, the pacing module 225 provides pacing therapy according to the secondary pacing for a first specified time duration. This first time duration follows the switch from the primary mode to the secondary mode and may be referred to as an A-V search interval. The A-V search interval may be measured in time (e.g., in ms) or by ventricular events (e.g., ten ventricular sensed or paced events). In certain examples, the pacing module 225 provides DDD/DDD(R) pacing using a first A-V delay (e.g., 150 ms). If a premature ventricular contraction (PVC) occurs the PVC may be counted the same as any other V-sense event.

At block 810, the pacing module 225 paces at least one ventricle using an extended A-V delay instead of the first A-V delay for a second time duration that follows the first time duration. The extended A-V delay is longer than the first A-V delay (e.g., 300 ms). In certain examples, the second duration is measured in cardiac cycles (e.g., eight cardiac cycles). The A-V delay is extended to search for intrinsic ventricular contractions.

At block 815, event detection module 230 determines whether an A-V conduction event occurs during the second duration. The event detection module 230 declares an A-V conduction event if an intrinsic ventricular contraction is sensed using the extended A-V delay. If the second time duration expires without an intrinsic ventricular contraction being sensed, the pacing module 225 returns, at block 805, to pacing the ventricle using the first A-V delay in the secondary mode. If an A-V conduction event occurs, the event detection module 230 then determines whether A-V conduction events are sustained according to a specified number of declared A-V conduction events occurring after the sensed intrinsic ventricular contraction. At block 820, the controller 220 includes a counter (Conduction Event Counter) that is incremented by the event detection module 230 when an intrinsic ventricular contraction occurs (i.e., a conduction event). In certain examples, the counter is initialized to zero after the first intrinsic ventricular contraction during the second time duration and incremented on subsequent intrinsic ventricular contractions (e.g., as detected at block 830).

At block 825, the event detection module 230 determines if the count of intrinsic ventricular contractions has reached a specified number of contractions. If not, the event detection module 230 continues searching for intrinsic ventricular contractions at block 830. If the count of intrinsic ventricular contractions reaches the specified count (e.g. twenty-five), sustained A-V conduction is declared and, at block 835, the pacing module 225 switches back to the primary pacing mode.

In order to return to the primary pacing mode, in some examples, a number of intrinsic ventricular events need to occur in order to switch back to the primary mode as long as a certain number of A-V block events don't occur during this period. If enough A-V block events occur, then A-V block continues to be deemed sustained. In certain examples, the pacing module 225 is configured for returning to pacing the ventricle using the first A-V delay in the secondary mode at block 805 if a specified number of A-V block events occur after the second time duration expires but before the specified number of declared A-V conduction events occur.

At block 840, the event detection module 230 determines whether an A-V block event occurred. The event detection module 230 may declare that an A-V block event occurred if a V-pace event occurs (e.g., because an extended A-V delay timer times out). At block 820, the controller 220 includes a counter (Block Event Counter) that is incremented by the event detection module 230 when an A-V block event is declared. The event detection module 230 may declare that A-V block events are sustained when X block events occur during the last Y cardiac cycles. If A-V block events are declared to be sustained before the specified number of A-V conduction events occur to declare A-V conduction events to be sustained, the pacing module 225 returns to pacing in the secondary mode using the first A-V delay at block 805.

In some examples, a clinician may want the device to stay in the secondary pacing mode when sustained A-V block events are declared. The controller 220 can be programmed to turn off the A-V search feature. The device will then remain in the secondary mode until it is reprogrammed, such as in a clinical setting for example.

In some examples, the device 200 includes a memory 240 that may be included in the controller or separate from the controller. When a pacing mode switch occurs, either from primary pacing mode to the secondary pacing mode or from secondary mode to primary mode, the controller stores an indication of at least one instance of a pacing mode switch in the memory.

In some examples, the device 200 includes an implantable cardiac signal sensing circuit. The cardiac signal sensing circuit may be the same or different from the cardiac contraction sensing circuit 205. The cardiac signal sensing circuit senses electrical cardiac signals associated with action potential signals of a heart. The action potentials propagate through the heart's electrical conduction system to excite various regions of myocardial tissue. The cardiac signal sensing circuit provides an electrical signal representative of such signals. Examples of cardiac signal sensing circuits include, without limitation, a subcutaneous ECG sensing circuit, an intracardiac electrogram (EGM) sensing circuit, and a wireless ECG sensing circuit. In a subcutaneous ECG sensing circuit, electrodes are implanted beneath the skin and the ECG signal obtained is referred to as subcutaneous ECG or far-field electrogram. In an intracardiac EGM circuit, at least one electrode is placed in or around the heart. A wireless ECG includes a plurality of electrodes to provide differential sensing of cardiac signals to approximate a surface ECG. Descriptions of wireless ECG systems are found in commonly assigned, co-pending U.S. patent application Ser. No. 10/795,126 by McCabe et al., entitled "Wireless ECG in Implantable Devices," filed on Mar. 5, 2004, which is incorporated herein by reference, including its description of a wireless ECG.

When a pacing mode switch occurs, the cardiac signal sensing circuit produces an electrogram representative of an intrinsic cardiac signal. The controller 220 stores EGM data in the memory 240 in association with the indication of a pacing mode switch. This can be viewed as a memory log entry. In some examples, a timestamp of when a mode switch occurred from the primary pacing mode to the secondary pacing mode is stored in memory. In some examples, if A-V conduction is declared to be restored and the pacing module 225 switches from the secondary pacing mode back to the primary pacing mode, the time duration that the device delivered pacing therapy according to the secondary mode is stored in memory.

In some examples, the device 200 includes a communication circuit 245 communicatively coupled to the controller 220. The controller 220 communicates wireless signals to a second device using the communication circuit 245. In some examples, the communication circuit 245 communicates the indication of a pacing mode switch to the second device. In some examples, the communication circuit 245 communicates at least one log entry in memory to the second device. The log entry includes at least one of a pacing mode switch indication, an EGM recorded when a pacing mode switch occurs, and a timestamp when the mode switch occurred. In certain examples, the log entry includes the time duration that the device 200 paced according to the secondary mode. In some examples, the second device includes a programmer for the device 200. In certain examples, the second device is communicatively coupled to a communication network, such as the internet or a mobile telephone network. The second device may communicate with the device 200 by using a third device, such as a repeater that is in the same room as the subject, for example.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A device comprising:
    at least one implantable cardiac contraction sensing circuit configured for providing a sensed contraction signal from an atrium and a sensed contraction signal from a ventricle;
    a timer circuit configured for providing a time duration of an atrial-atrial (A-A) interval between successive atrial contractions, a ventricular-ventricular (V-V) interval between successive ventricular contractions, and an atrial-ventricular (A-V) interval between an atrial contraction and a same cardiac cycle ventricular contraction;
    an electrical stimulation circuit configured to provide pacing electrical stimulation energy to at least one implantable electrode in the atrium and at least one implantable electrode in the ventricle; and
    a controller communicatively coupled to the cardiac contraction sensing circuit, the timer circuit, and the electrical stimulation circuit, wherein the controller includes:
    an event detection module configured for determining whether atrial-ventricular (A-V) block events are sustained over multiple cardiac cycles; and
    a pacing module configured for:
        providing bradycardia pacing therapy according to a primary pacing mode including:
            pacing at least one atrium, at an atrial pacing interval that is computed independently of any event occurring in the ventricle, when an A-A interval exceeds an atrial lower rate limit (LRL) interval; and
            concurrently providing pacing to at least one ventricle while in the same primary pacing mode, at a ventricular pacing interval that is computed independently of any event occurring in the atrium, when a V-V interval exceeds a ventricular LRL interval, wherein the ventricular LRL interval is longer than the atrial LRL interval; and
        switching the pacing therapy to a secondary pacing mode if A-V block events are sustained over multiple cardiac cycles, wherein the secondary pacing mode includes pacing the at least one ventricle when an atrial-ventricular contraction (A-V) interval exceeds a first A-V delay interval.

2. The device of claim 1, wherein the event detection module includes an A-V block event counter and the event detection module is configured for declaring A-V block events to be sustained when an A-V blocking event is declared in X out of Y consecutive V-V intervals, wherein X and Y are integers and X is less than or equal to Y.

3. The device of claim 1, wherein the event detection module is configured for declaring an atrial-ventricular (A-V) block event if at least one of:
   the ventricular LRL interval is exceeded without a sensed ventricular event occurring; and
   a V-V interval is sensed that is longer than the atrial LRL interval by a specified threshold value and shorter than the ventricular LRL interval.

4. The device of claim 1, wherein the event detection module is configured for determining whether A-V conduction events are sustained over multiple cardiac cycles; and
   wherein the pacing module is configured for switching the pacing therapy from the secondary pacing mode to the primary pacing mode if A-V conduction events are sustained.

5. The device of claim 4, wherein the pacing module is configured for:
   pacing according to the secondary mode using the first A-V delay for a first time duration after switching from the primary mode; and
   pacing the ventricle according to an extended A-V delay interval, instead of the first A-V delay interval, for a second time duration that follows the first time duration, wherein the extended A-V delay interval is longer than the first A-V delay interval; and wherein the event detection module is configured for:
   declaring an A-V conduction event if an intrinsic ventricular contraction is sensed during the second time duration; and
   determining whether A-V conduction events are sustained according to a specified number of declared A-V conduction events occurring after the sensed intrinsic ventricular contraction.

6. The device of claim 5, wherein the pacing module is configured for returning to pacing the ventricle using the first A-V delay in the secondary mode if the second time duration expires without an intrinsic ventricular contraction being sensed.

7. The device of claim 5, wherein the pacing module is configured for returning to pacing the ventricle using the first A-V delay in the secondary mode if a XV-paces occur during Y cardiac cycles after the second time duration expires but before the specified number of declared A-V conduction events occur, where X and Y are integers and X is less than or equal to Y.

8. The device of claim 5, wherein the controller includes a counter, and wherein the pacing module is configured to determine the first time duration and the second time duration using at least one specified count of one or more cardiac cycles.

9. The device of claim 4, including a memory communicatively coupled to the controller, the memory configured to store at least one indication of at least one instance of a pacing mode switch in the memory when at least one of a pacing mode switch from the primary pacing mode to the secondary pacing mode occurs and a pacing mode switch from the secondary pacing mode to the primary pacing mode occurs.

10. The device of claim 9, including an implantable cardiac signal sensing circuit communicatively coupled to the controller, wherein the cardiac signal sensing circuit is configured for producing an electrogram representative of an intrinsic cardiac signal, and wherein the controller is configured for storing electrogram data in the memory association with the at least one indication.

11. The device of claim 9, including a communication circuit communicatively coupled to the controller, wherein the communication circuit is configured to communicate the indication to a second device.

12. The device of claim 1, including an activity sensor, and wherein the pacing module is configured for pacing an atrium when an A-A interval exceeds an activity sensor indicated atrial rate interval.

13. The device of claim 12, wherein the pacing module is configured for pacing a ventricle, without regard to any event occurring in the atrium, when a V-V interval exceeds an activity sensor indicated ventricular rate interval, wherein the activity sensor indicated ventricular rate interval is longer than the activity sensor indicated atrial rate interval.

14. The device of claim 12, wherein the event detection module is configured for declaring an atrial-ventricular (A-V) block event if at least one of the following events occurs:
   the ventricular LRL interval is exceeded without a sensed ventricular event occurring;
   a ventricular contraction (V-V) interval is sensed that is longer than the atrial LRL and shorter than the ventricular LRL; and
   a ventricular contraction (V-V) interval is sensed that is longer than an activity sensor indicated atrial rate interval by a specified threshold value and shorter than the ventricular LRL interval.

15. The device of claim 12, wherein the event detection module is configured for declaring an atrial-ventricular (A-V) block event if a ventricular contraction (V-V) interval is sensed that is longer than an activity sensor indicated atrial rate interval by a specified threshold value and shorter than an activity sensor indicated ventricular lower rate interval.

16. A method comprising:
   sensing, using an implantable medical device (IMD), atrial-atrial (A-A) intervals between successive atrial contractions in an atrium and ventricular-ventricular (V-V) intervals between successive ventricular contractions in a ventricle;
providing bradycardia pacing therapy according to a primary pacing mode, the providing pacing therapy including:
   pacing at least one atrium, at an atrial pacing interval that is computed independently of any event occurring in the ventricle, when an A-A interval exceeds an atrial lower rate limit (LRL) interval; and
   concurrently pacing at least one ventricle while in the same primary pacing mode, at a ventricular pacing interval that is computed independently of any event occurring in the atrium, when a V-V interval exceeds a ventricular LRL interval, wherein the ventricular LRL interval is longer than the atrial LRL interval;
   determining with the IMD whether atrial-ventricular (A-V) block events are sustained over multiple cardiac cycles; and
   switching the pacing therapy to a secondary pacing mode if A-V block events are sustained over multiple cardiac cycles, wherein the secondary pacing mode includes pacing the ventricle when an atrial-ventricular (A-V) interval between an atrial contraction and a same cardiac cycle ventricular contraction exceeds a first A-V delay interval.

17. The method of claim 16, wherein determining whether A-V block events are sustained includes declaring A-V block events to be sustained when an A-V block event is declared in X out of Y consecutive V-V intervals, wherein X and Y are integers and X is less than or equal to Y.

18. The method of claim 16, wherein determining whether A-V block events are sustained includes declaring an A-V block event if at least one of:
   the ventricular LRL interval is exceeded without a sensed ventricular event occurring during the ventricular LRL interval; and
   a V-V interval is sensed that is longer than the atrial LRL interval and shorter than the ventricular LRL interval.

19. The method of claim 16, including:
   determining whether A-V conduction events are sustained over multiple cardiac cycles; and
   switching the pacing therapy from the secondary pacing mode to the primary pacing mode if A-V conduction events are sustained.

20. The method of claim 19, wherein determining whether A-V conduction events are sustained includes:
   pacing using the secondary pacing mode using the first A-V delay for a first time duration after switching from the primary mode;
   pacing the at least one ventricle using an extended A-V delay interval, instead of the first A-V delay interval, for a second time duration following the first time duration, wherein the extended A-V delay interval is longer than the first A-V delay interval;
   declaring an A-V conduction event if an intrinsic ventricular contraction is sensed during the second time duration; and
   declaring A-V conduction events to be sustained when there are a specified number of declared A-V conduction events after the second time duration.

21. The method of claim 20, including returning to pacing the at least one ventricle using the first A-V delay in the secondary pacing mode if the second time duration expires without an intrinsic ventricular contraction being sensed during the second time duration.

22. The method of claim 20, including returning to pacing the ventricle using the first A-V delay in the secondary mode if a specified number of A-V block events are detected after the second time duration expires but before the specified number of declared A-V conduction events occur.

23. The method of claim 20, wherein the first time duration and the second time duration are defined using at least one specified count of one or more cardiac cycles.

24. The method of claim 19, including storing an indication of at least one instance of a pacing mode switch in response to at least one occurrence of a pacing mode switch from the primary pacing mode to the secondary pacing mode or at least one occurrence of a pacing mode switch from the secondary pacing mode to the primary pacing mode.

25. The method of claim 24, including storing electrogram data in association with the indication.

26. The method of claim 24, including communicating the indication from a cardiac function management device to an external device.

27. The method of claim 16, wherein the primary pacing mode includes pacing at least one atrium when an A-A interval exceeds an activity sensor indicated atrial rate interval.

28. The method of claim 27, wherein the primary pacing mode includes pacing a ventricle, without regard to any event occurring in the atrium, when a V-V interval exceeds an activity sensor indicated ventricular rate interval, wherein the activity sensor indicated ventricular rate interval is longer than the activity sensor indicated atrial rate interval.

29. The method of claim 27, wherein determining whether A-V block events are sustained over multiple cardiac cycles includes:
   declaring an A-V block event if at least one of the following events occurs:
      the ventricular LRL interval is exceeded without a sensed ventricular event occurring during the ventricular LRL interval;
      a sensed V-V interval is longer than the atrial LRL interval and shorter than the ventricular LRL interval; and
      a sensed V-V interval is longer than an activity sensor indicated atrial rate interval by a specified threshold value and shorter than the ventricular LRL interval.

30. The method of claim 27, wherein determining whether A-V block events are sustained over multiple cardiac cycles includes declaring an A-V block event if a ventricular contraction (V-V) interval is sensed that is longer than an activity sensor indicated atrial rate interval by a specified threshold value and shorter than an activity sensor indicated ventricular lower rate interval.

31. An apparatus comprising:
   means for sensing atrial-atrial (A-A) intervals between successive atrial contractions in an atrium and ventricular-ventricular (V-V) intervals between successive ventricular contractions in a ventricle;
   means for providing bradycardia pacing therapy according to a primary pacing mode, the providing pacing therapy including:
   means for pacing at least one atrium, at an atrial pacing interval that is computed independently of any event occurring in the ventricle, when an A-A interval exceeds an atrial lower rate limit (LRL) interval; and
   means for concurrently providing pacing to at least one ventricle while in the same primary pacing mode, at a ventricular pacing interval that is computed independently of any event occurring in the atrium, when a V-V interval exceeds a ventricular LRL interval, wherein the ventricular LRL interval is longer than the atrial LRL interval;
   means for determining whether atrial-ventricular (A-V) block events are sustained over multiple cardiac cycles; and
   means for switching the pacing therapy to a secondary pacing mode if A-V block events are sustained over multiple cardiac cycles, wherein the secondary pacing mode includes pacing the ventricle when an atrial-ventricular (A-V) interval between an atrial contraction and a same cardiac cycle ventricular contraction exceeds an first A-V delay interval.

* * * * *